(12) United States Patent
Leanna et al.

(10) Patent No.: US 8,109,988 B2
(45) Date of Patent: *Feb. 7, 2012

(54) STENTS WITH ATTACHED LOOPED ENDS

(75) Inventors: Gary J. Leanna, Holden, MA (US); Paul K. Norton, Lunenburg, MA (US); Peter Brady, Galway (IE); Dean Molloy, Kilrush Hollymount (IE); Michael E. Zupkofska, Rockland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/649,843

(22) Filed: Dec. 30, 2009

(65) Prior Publication Data

US 2010/0161034 A1 Jun. 24, 2010

Related U.S. Application Data

(63) Continuation of application No. 10/852,495, filed on May 24, 2004, now Pat. No. 7,655,039.

(60) Provisional application No. 60/472,929, filed on May 23, 2003.

(51) Int. Cl.
*A61F 2/82* (2006.01)

(52) U.S. Cl. ....................................... 623/1.15

(58) Field of Classification Search ........ 623/1.15–1.22, 623/1.3–1.35, 1.36, 1.51, 1.53
See application file for complete search history.

(56) References Cited

U.S. PATENT DOCUMENTS

| 4,300,244 | A | 11/1981 | Bokros |
| 4,512,338 | A | 4/1985 | Balko et al. |
| 4,553,545 | A | 11/1985 | Maass et al. |
| 4,572,186 | A | 2/1986 | Gould et al. |
| 4,580,568 | A | 4/1986 | Gianturco |
| 4,665,771 | A | 5/1987 | Mitchell |
| 4,665,918 | A | 5/1987 | Garza et al. |
| 4,681,110 | A | 7/1987 | Wiktor |
| 4,732,152 | A | 3/1988 | Wallsten et al. |
| 4,733,665 | A | 3/1988 | Palmaz |
| 4,740,207 | A | 4/1988 | Kreamer |
| 4,762,128 | A | 8/1988 | Rosenbluth |

(Continued)

FOREIGN PATENT DOCUMENTS

WO 0135864 5/2001

(Continued)

OTHER PUBLICATIONS

European Search Report.

*Primary Examiner* — Elizabeth Houston
(74) *Attorney, Agent, or Firm* — Vidas, Arrett & Steinkraus

(57) ABSTRACT

An open frame prosthesis is formed with looped end terminations at its proximal and distal ends. At one end of the prosthesis, the filaments or strands are welded together in pairs to form strand couplings. A plurality of loop segments are connected to the strand couplings, one loop segment for each pair of adjacent strand couplings. In one version of the prosthesis, strands at the opposite end are bent to form looped ends. In another version, loop segments are connected to pairs of strand couplings at both ends of the prosthesis. The loop segments can be connected to the couplings by welding, fusion bonds, or tubes, which are either crimped or heat shrunk.

7 Claims, 5 Drawing Sheets

U.S. PATENT DOCUMENTS

| | | |
|---|---|---|
| 4,768,507 A | 9/1988 | Fischell et al. |
| 4,795,458 A | 1/1989 | Regan |
| 4,830,003 A | 5/1989 | Wolff et al. |
| 4,848,343 A | 7/1989 | Wallsten et al. |
| 4,875,480 A | 10/1989 | Imbert |
| 4,878,906 A | 11/1989 | Lindemann et al. |
| 4,886,062 A | 12/1989 | Wiktor |
| 4,893,623 A | 1/1990 | Rosenbluth |
| 4,907,336 A | 3/1990 | Gianturco |
| 4,913,141 A | 4/1990 | Hillstead |
| 4,950,227 A | 8/1990 | Savin et al. |
| 4,969,458 A | 11/1990 | Wiktor |
| 4,969,890 A | 11/1990 | Sugita et al. |
| 4,990,155 A | 2/1991 | Wilkoff |
| 4,998,539 A | 3/1991 | Delsanti |
| 5,002,560 A | 3/1991 | Machold et al. |
| 5,026,377 A | 6/1991 | Burton et al. |
| 5,034,001 A | 7/1991 | Garrison et al. |
| 5,035,706 A | 7/1991 | Giantureo et al. |
| 5,037,392 A | 8/1991 | Hillstead |
| 5,037,427 A | 8/1991 | Harada et al. |
| 5,041,126 A | 8/1991 | Gianturco |
| 5,059,166 A | 10/1991 | Fischell et al. |
| 5,061,275 A | 10/1991 | Wallsten et al. |
| 5,064,435 A | 11/1991 | Porter |
| 5,071,407 A | 12/1991 | Termin et al. |
| 5,078,720 A | 1/1992 | Burton et al. |
| 5,089,005 A | 2/1992 | Harada |
| 5,089,006 A | 2/1992 | Stiles |
| 5,092,877 A | 3/1992 | Pinchuk |
| 5,108,416 A | 4/1992 | Ryan et al. |
| 5,123,917 A | 6/1992 | Lee |
| 5,135,517 A | 8/1992 | McCoy |
| 5,158,548 A | 10/1992 | Lau et al. |
| 5,163,952 A | 11/1992 | Froix |
| 5,163,958 A | 11/1992 | Pinchuk |
| 5,171,262 A | 12/1992 | MacGregor |
| 5,183,085 A | 2/1993 | Timmermans |
| 5,192,297 A | 3/1993 | Hull |
| 5,197,978 A | 3/1993 | Hess |
| 5,201,757 A | 4/1993 | Heyn et al. |
| 5,222,969 A | 6/1993 | Gillis |
| 5,222,971 A | 6/1993 | Willard et al. |
| 5,226,913 A | 7/1993 | Pinchuk |
| 5,234,457 A | 8/1993 | Andersen |
| 5,242,451 A | 9/1993 | Harada et al. |
| 5,256,146 A | 10/1993 | Ensminger et al. |
| 5,258,020 A | 11/1993 | Froix |
| 5,263,964 A | 11/1993 | Purdy |
| 5,282,823 A | 2/1994 | Schwartz et al. |
| 5,282,824 A | 2/1994 | Gianturco |
| 5,290,295 A | 3/1994 | Querals et al. |
| 5,304,200 A | 4/1994 | Spaulding |
| 5,306,294 A | 4/1994 | Winston et al. |
| 5,354,308 A | 10/1994 | Simon et al. |
| 5,354,309 A | 10/1994 | Schnepp-Pesch |
| 5,372,600 A | 12/1994 | Beyar et al. |
| 5,378,239 A | 1/1995 | Termin et al. |
| 5,395,390 A | 3/1995 | Simon et al. |
| 5,403,341 A | 4/1995 | Solar |
| 5,405,377 A | 4/1995 | Cragg |
| 5,411,507 A | 5/1995 | Heckele |
| 5,411,552 A | 5/1995 | Andersen et al. |
| 5,415,664 A | 5/1995 | Pinchuk |
| 5,443,496 A | 8/1995 | Schwartz et al. |
| 5,453,090 A | 9/1995 | Martinez et al. |
| 5,456,694 A | 10/1995 | Marin et al. |
| 5,474,563 A | 12/1995 | Myler et al. |
| 5,478,349 A | 12/1995 | Nicholas |
| 5,484,444 A | 1/1996 | Braunschweiler et al. |
| 5,496,277 A | 3/1996 | Termin et al. |
| 5,507,771 A | 4/1996 | Gianturco |
| 5,522,883 A | 6/1996 | Slater et al. |
| 5,534,007 A | 7/1996 | St. Germain et al. |
| 5,554,181 A | 9/1996 | Das |
| 5,591,230 A | 1/1997 | Horn et al. |
| 5,690,643 A | 11/1997 | Wijay |
| 5,702,364 A | 12/1997 | Euteneuer et al. |
| 5,716,393 A | 2/1998 | Lindenberg et al. |
| 5,772,669 A | 6/1998 | Vrba |
| 5,800,519 A | 9/1998 | Sandock |
| 5,807,327 A | 9/1998 | Green et al. |
| 5,824,041 A | 10/1998 | Lenker et al. |
| 5,833,707 A | 11/1998 | McIntyre et al. |
| 5,836,965 A | 11/1998 | Jendersee et al. |
| 5,935,135 A | 8/1999 | Bramfitt et al. |
| 5,948,017 A | 9/1999 | Taheri |
| 5,954,729 A | 9/1999 | Bachmann et al. |
| 6,001,123 A | 12/1999 | Lau |
| 6,007,574 A | 12/1999 | Pulnev et al. |
| 6,017,362 A | 1/2000 | Lau |
| 6,027,529 A | 2/2000 | Roychowdhury et al. |
| 6,053,941 A | 4/2000 | Lindenberg et al. |
| 6,077,295 A | 6/2000 | Limon et al. |
| 6,102,940 A | 8/2000 | Robichon et al. |
| 6,120,522 A | 9/2000 | Vrba et al. |
| 6,241,757 B1 | 6/2001 | An et al. |
| 6,258,098 B1 | 7/2001 | Taylor et al. |
| 6,258,099 B1 | 7/2001 | Mareiro |
| 6,264,689 B1 * | 7/2001 | Colgan et al. ............ 623/1.22 |
| 6,295,714 B1 | 10/2001 | Roychowdhury et al. |
| 6,302,893 B1 | 10/2001 | Limon et al. |
| 6,309,415 B1 | 10/2001 | Pulnev et al. |
| 6,352,553 B1 | 3/2002 | van der Burg et al. |
| 6,398,807 B1 | 6/2002 | Chouinard et al. |
| 6,419,694 B1 | 7/2002 | Sandock |
| 6,468,301 B1 | 10/2002 | Amplatz et al. |
| 6,514,282 B1 | 2/2003 | Inoue |
| 6,576,006 B2 | 6/2003 | Limon et al. |
| 6,623,518 B2 | 9/2003 | Thompson et al. |
| 6,641,608 B1 | 11/2003 | Pulnev |
| 2001/0007082 A1 | 7/2001 | Dusbabek et al. |
| 2004/0098099 A1 * | 5/2004 | McCullagh et al. ......... 623/1.15 |
| 2009/0198315 A1 | 8/2009 | Boudjemline |

FOREIGN PATENT DOCUMENTS

| | | |
|---|---|---|
| WO | WO 0135864 A1 | 5/2001 |
| WO | 0154614 A2 | 8/2001 |
| WO | 0154614 A3 | 8/2001 |
| WO | 2004045461 | 6/2004 |
| WO | WO 2004045461 A1 | 6/2004 |
| WO | WO 2005110286 A1 | 11/2005 |

* cited by examiner

STENTS WITH ATTACHED LOOPED ENDS

CROSS-REFERENCE TO RELATED APPLICATIONS

This application is a continuation of U.S. patent application Ser. No. 10/852,495, filed May 24, 2004 now U.S. Pat. No. 7,655,039, which claims the benefit of U.S. Provisional Application No. 60/472,929 entitled "Stents With Welded Looped Ends," filed May 23, 2003, the contents of all of which are incorporated herein by reference.

FIELD OF THE INVENTION

The present invention relates to stents and other body insertable devices of open frame construction, and more particularly to radially expandable or radially self-expanding prostheses.

BACKGROUND OF THE INVENTION

A variety of treatment and diagnostic procedures involve the use of devices intraluminally implantable into the body of the patient. Among these devices are stents, such as disclosed in U.S. Pat. No. 4,655,771 (Wallsten). This type of prosthesis, shown in FIG. 1, is a tubular, braided structure formed of thread elements wound helically in opposite directions. The stent is shown in a relaxed state, i.e. in the configuration assumed when the stent is subject to no external stress. The stent is elastically compressible to a reduced-radius, axially elongated state to facilitate an intraluminal delivery of the stent to an intended treatment site. At the site, the stent is released for radial self-expansion into contact with surrounding tissue, for example a blood vessel wall. The stent does not fully expand, but instead remains under a slight elastic compression, so that an internal elastic restoring force tends to anchor the stent within the vessel, and maintain vessel patency.

The thread elements, also called strands or filaments, form multiple intersections or crossing points, each including a pair of oppositely directed strands. At each end of the stent, oppositely directed strands are connected in pairs to form end terminations or strand couplings. The strands can be formed of metal, in which case the end terminations can be formed by welding the strands or by twisting the pairs of strands together, preferably augmented with welds. Alternatively, the strands can be formed of polymeric materials, with end terminations formed by fusing the strands or boding them with an adhesive.

As an alternative to self-expanding stents, a malleable metal such as tantalum can be wound or braided into a plastically deformable prosthesis. This device is capable of maintaining a reduced-radius state on its own to facilitate delivery, but requires a balloon or other implement to expand the prosthesis into contact with surrounding tissue at the treatment site.

FIG. 2 illustrates part of a prosthesis formed according to an alternative construction in which the strands are wound instead of braided, to form generally hexagonal cells. Adjacent cells have coextensive regions, along which pairs of the strands are wrapped helically about one another. This construction is further illustrated and explained in U.S. Pat. No. 5,800,519 (Sandock).

FIG. 3 illustrates a prosthesis formed according to another construction, illustrated and discussed in U.S. Pat. No. 6,264,689 (Colgan). Like the stent in FIG. 2, this stent features structural strands wound to form multiple helical cells. However, it differs from the device of FIG. 2, in that at some of the junctions of strands, the strands simply cross one another, rather than being twisted helically about one another.

At a distal end of the prosthesis in FIG. 3, the strands are bent to form a plurality of loops 1. These loops form relatively flexible, blunt end terminations, desirable because they more readily adjust to features of the body lumen in which the prosthesis is deployed, and they present minimal risk of injury to the surrounding tissue. Conversely, at the proximal end, pairs of strands are twisted together and ball welded at the ends, to form proximal end terminations 2.

The devices in FIGS. 1 and 2 may also be formed with distal and proximal end terminations comprising bends and twisted pairs, respectively. Alternatively, any of these devices may be formed with twisted end terminations at both the proximal and distal ends. As a further alternative, terminations at the proximal end, or at both ends, may be formed by welding the pairs of strands together, without twisting.

In any event, while these stents are well suited for a variety of procedures, the welded or twisted end terminations are disadvantageous. As compared to the rest of the prosthesis, the welded or twisted end terminations are relatively stiff and rigid, and thus more likely to poke surrounding tissue, rather than bend to accommodate the tissue. Because of the abrupt ends of the welded or twisted end terminations, the poking occasioned by their relative stiffness presents a risk of damage to tissue. Consequently, any positional adjustment of a deployed stent, particularly in the direction that the welded or twisted end terminations extend, is difficult. Another problem encountered with the twisted or welded end terminations is that adjacent twisted wire pairs may interlock when the stent is radially compressed into the delivery state, and then interfere with radial expansion of the stent at a treatment site.

When the stent or other prosthesis is constructed by bending the strands at its distal end, the situation is improved somewhat by limiting the foregoing difficulties to the proximal side. While they are reduced, these difficulties remain, most notably to prevent any substantial proximal repositioning of a deployed stent. Further, even the looped distal end of such device presents a problem that can limit its use. In particular, radial contraction of the device requires each loop to bend, primarily at its distal apex. The extent of radial reduction is limited by the extent to which each loop can be bent.

Therefore, it is an object of the present invention to provide a prosthesis of open frame construction with blunt, flexible end terminations at both of its opposite ends, to permit movement of the deployed prosthesis relative to surrounding tissue in either axial direction, with minimal risk of trauma to the tissue.

Another object is to provide a prosthesis with looped end terminations that permit radial compression of the prosthesis to a smaller diameter for intraluminal delivery.

A further object is to provide a process for fabricating a stent with the elongate strands or strand segments selectively shaped at one or both ends of the stent to provide relatively blunt and flexible end terminations.

Yet another object is to provide a stent or other prosthesis that is more readily adjustable and retrievable after its deployment in a blood vessel or other body lumen.

SUMMARY OF THE INVENTION

To achieve the foregoing objects and others, there is provided an implantable prosthesis. The prosthesis includes a plurality of elongate strands cooperating to form an open-frame tubular structure radially expandable and contractible between an enlarged-radius state and a reduced-radius state. Different ones of the elongate strands are integrally coupled to one another along respective end regions thereof to form a plurality of strand couplings along a selected end of the tubular structure. A closure member is connected to a pair of associated strand couplings, and extends between the associated strand couplings to form a loop segment directed axially outwardly from the associated strand couplings.

In a preferred arrangement, each of the strand couplings is formed by joining two of the strands along their respective end regions, the strands form an even number of strand couplings, and the number of closure members is equal to one-half the number of strand couplings. Each closure member is connected to a different pair of the couplings; i.e. one end termination loop for every four strand ends.

For comparison, when the looped end terminations are formed by bending the strands as shown at 1 in FIG. 3, twice as many looped end terminations are required. Thus, looped end terminations formed according to the invention, although larger than the conventional looped end terminations, permit a similarly sized stent to be radially contracted to a smaller size, due to the lower number of looped end terminations.

In one advantageous form of the prosthesis, each pair of associated strand couplings includes a first strand coupling in which the ends of the coupled strands substantially coincide, and a second strand coupling in which one of the strands extends beyond the other to provide a strand extension of a predetermined length. The strand extension is selectively shaped and connected to the first strand coupling, preferably by welding, to provide the loop segment.

Other suitable means for connecting the closure members and strand couplings include fusion bonds, adhesives, and tubes surrounding adjacent portions of the closure member and strand coupling.

Preferably, each closure member is somewhat U-shaped, comprising opposite legs, each coupled to one of the paired strand couplings, and a medial region between the two legs. The medial region can be shaped to incorporate two inclined side sections and a curved apex between the side sections. As the tubular structure is radially contracted, each closure member tends to bend primarily at the apex, and along regions of slight curvature between the side sections and legs.

While shown and described primarily with braided and wound tubular structures, end closure members in accordance with the present invention can be employed to enhance virtually any open-frame structure having strand couplings at one of its ends, to render that end more flexible and reduce the risk of trauma to surrounding tissue.

Another aspect of the invention is a body implantable device, including a plurality of elongate strands wound to form an open-frame tubular body radially expandable and contractible between enlarged-radius and reduced-radius states. At one end of the tubular body, the strands are coupled integrally with respect to one another to form a plurality of strand end couplings arranged circumferentially about the selected end. A plurality of closure members are individually associated with pairs of the strand end couplings. Each closure member is connected to its associated pair of the couplings, and extends from a first one of the couplings to a second one of the couplings to form a loop segment directed axially outwardly from the associated pair.

Another aspect of the present invention is a process for forming a body implantable device with at least one atraumatic end, including: winding a plurality of elongate structural strands to form an open-frame tubular structure having first and second opposite ends; along a first one of said opposite ends, integrally coupling different ones of the elongate structural strands together along respective end regions thereof to form a plurality of strand couplings, wherein each of the strand couplings includes at least two of the strands; and shaping an elongate strand segment into a loop segment having an arcuate region, and forming a connection of the strand segment with an associated pair of the strand couplings, with the arcuate region disposed axially outwardly of the associated strand couplings.

Thus in accordance with the present invention, a stent or other open-frame prosthesis is fashioned with flexible, blunt, atraumatic ends, so that after its deployment in a body lumen, the device is movable without the risk of injury to surrounding tissue. As compared to similarly sized devices with conventional looped end construction, devices constructed according to the invention are compressible radially into smaller diameters to facilitate their intraluminal delivery. The looped end terminations described herein can be formed at either end or both ends of stents and other open-frame prostheses.

BRIEF DESCRIPTION OF THE DRAWINGS

For a further understanding of the above and other features and advantages, reference is made to the following detailed description and to the drawings, in which.

DETAILED DESCRIPTION OF THE PREFERRED EMBODIMENTS

Figure 1:
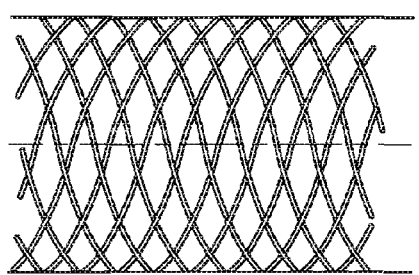
FIG. 1 is a side view of a conventional braided stent.

Turning now to the drawings, there is shown in FIG. 1 a stent 16 fabricated according to the present invention, and part of a device 18 used to intraluminally deliver the stent to an intended treatment site and deploy the stent at the treatment site.

The device includes an elongate, flexible outer catheter 20 having a distal end region 22, along which the outer catheter surrounds stent 16 and maintains the stent in a reduced-radius, axially elongated delivery state to facilitate an intraluminal delivery of the stent to the treatment site.

Stent 16 is contained within a lumen 24, which runs substantially the entire length of the outer catheter. An inner catheter 26, contained in the lumen, extends lengthwise along the outer catheter and is moveable axially relative to the outer catheter. A deployment member 28 is fixed to inner catheter 26, proximally of stent 16. Inner catheter 26 includes a lumen (not shown) to accommodate a guidewire 30, which is used to guide the inner and outer catheters to the treatment site. When outer catheter 20 is moved proximally relative to inner catheter 26, the deployment member is encountered by the proximal end of the stent, whereupon further proximal movement of the outer catheter progressively releases the stent from the outer catheter, allowing the stent to radially self-expand into contact with surrounding tissue.

Stent 16 is composed of oppositely directed helically wound strands or filaments 32 that intersect one another to form multiple intersections or crossing points. Strands 32 are interbraided in a one-over-one-under pattern. At the distal end of stent 16, strands 32 are bent to form distal end loops 33. Preferably the strands are formed of a superelastic alloy of titanium and nickel sold under the brand name Nitinol. Other suitable strand materials include cobalt-based alloys such as those sold under the brand names Elgiloy or Phynox, MP35N alloy, and certain stainless steels. Suitable nonmetallic alternatives include polymers, for example polyester and polyethylene terephthalate (PET).

Figure 5:
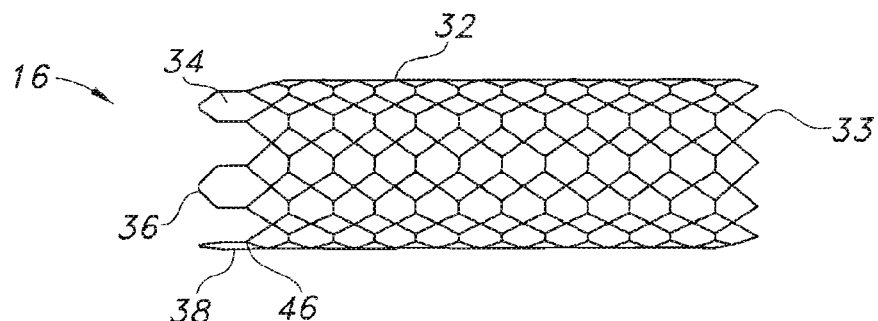
FIG. 5 is a side view of the stent of FIG. 4, in a relaxed state.

Strands 32 are resilient, and when maintained as shown in FIG. 1 store an elastic restoring force. When released from outer catheter 20, stent 16 self-expands under the restoring force, toward a normal or relaxed state shown in FIG. 5 that stent 16 assumes when under no external stress. As a result of its braided construction and helical strand shapes, stent 16 shortens axially as it expands radially. When the deployed in a blood vessel or other body lumen, stent 16 engages surrounding tissue before it expands fully to the relaxed state. Thus, the deployed stent exerts a radially outward force against the tissue that tends to anchor the stent at the treatment site.

Figure 2:
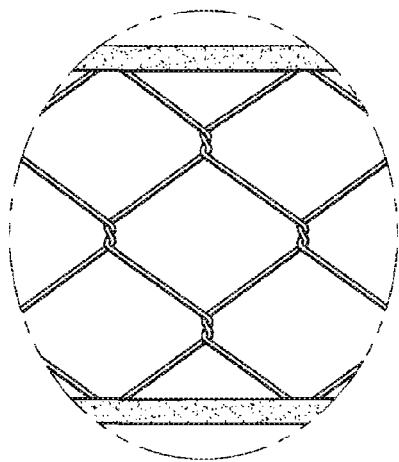
FIGS. 2 and 3 illustrate known alternative open frame prosthesis constructions.
Figure 3:
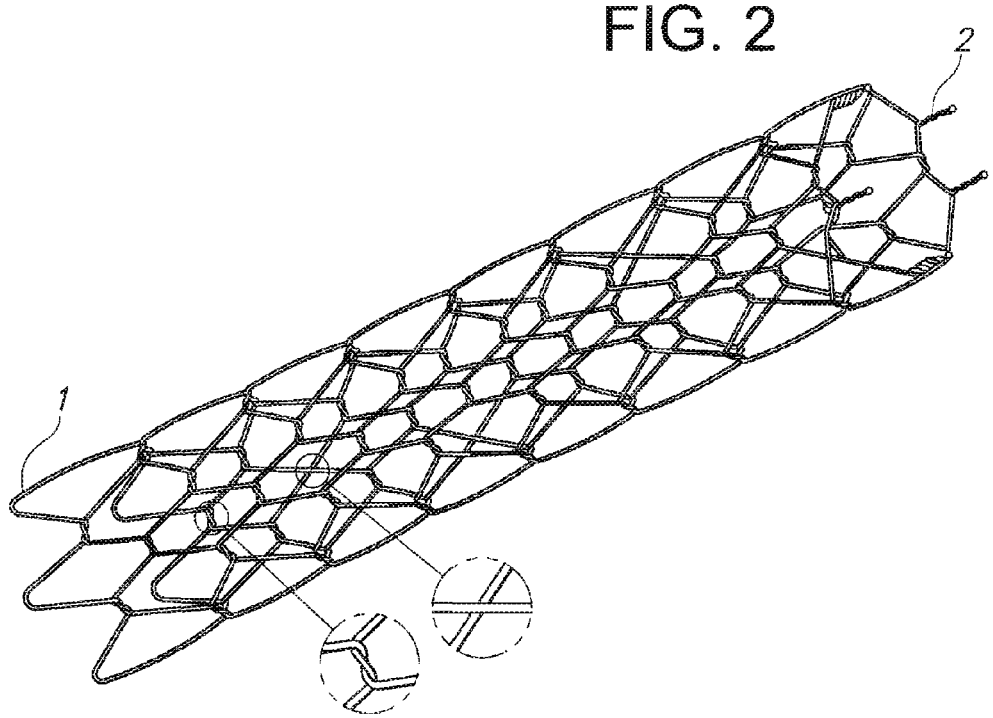
Figure 4:
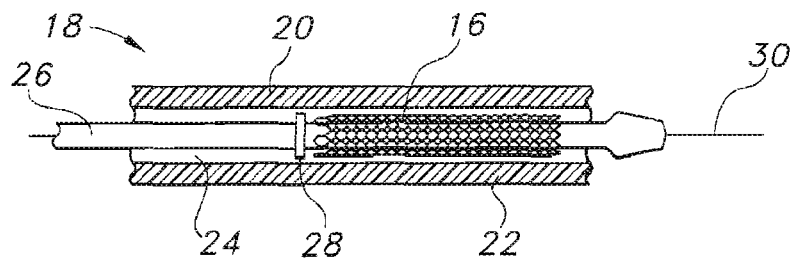
FIG. 4 is a side view, partially in section, showing a braided stent constructed according to the present invention, contained within a deployment and delivery device.

One of the challenges to the physician using device 18 is to accurately place the stent. Accurate placement is made more difficult by the axial shortening of the stent as it enlarges radially. Once the stent is fully deployed, it is contiguous with and frequently partially embedded into the surrounding tissue. As a result, it is difficult to adjust the position of the stent to correct a less than accurate placement. With prostheses constructed as shown in FIGS. 1-3, proximal stent adjustment is particularly difficult because of the stiff welded and/or twisted strand couplings with abrupt proximal ends that present the risk of injury to tissue.

Figure 6:
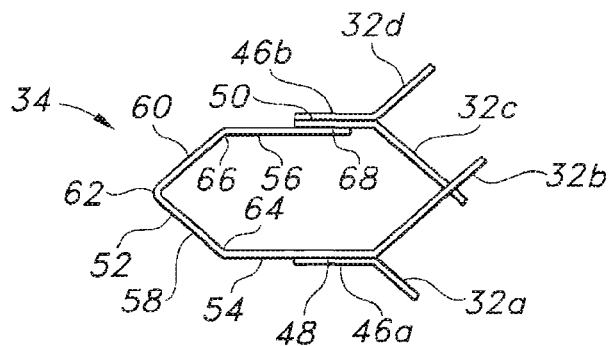
FIG. 6 is an enlarged view of one end of the stent.

In accordance with the present invention, the proximal end of stent 16 is formed with a series of loop segments. Specifically, six loop segments 34-44 are formed in conjunction with twelve strand junctions or couplings 46. Each loop segment acts as a closure member, cooperating with its associated pair of strand couplings and the coupled strands to form a closed loop end termination. Each loop segment is formed with an extension of one of the coupled strands. For example, FIG. 6 shows a strand junction 46a including strands 32a and 32b, coupled to each other by a weld 48. Similarly, strands 32c and 32d are joined by a weld 50 to form a strand junction 46b.

Strand 32b is longer than the other strands by a predetermined length, to provide a proximal strand extension or portion 52 extending beyond the other strands, which is shaped to provide loop segment 34. Loop segment 34 has several discrete elements, including opposed axially extending legs 54 and 56, opposite inclined linear side sections 58 and 60, a curved proximal end apex 62, and a pair of arcuate sections 64 and 66, each between one of the legs and side sections. A portion of leg 56 is axially aligned with junction 46b, and is connected to that coupling by a weld 68. The remaining loop segments 34-44 are formed in the same manner.

Stent 16 after deployment can be moved proximally along the body lumen without the risk of trauma to the surrounding tissue. Apex 62 and its counterparts on the other loop segments provide smooth, rounded, blunt proximal end terminations with no tendency to poke or cut into tissue as the stent is moved. Also, the loop segments are considerably more flexible than the strand end junctions, regardless of whether the strands are twisted. This is primarily due to strands 32, which are bendable about tangential axes both proximally and distally of junctions 46 to carry apex 62 and its counterparts radially inward. This affords a localized (proximal) radial contraction of the stent to facilitate pulling the stent proximally along the lumen while the majority of the stent remains in contact with surrounding tissue.

Apex 62 further is bendable about radial axes, to bring the legs and side sections closer to one another during radial contraction. Arcuate sections 64 and 66 also are bendable about radial axes, although unlike the apex, they bend in the direction of increasing radii of curvature during radial contraction of the stent. As a result, legs 54 and 56 tend to retain their axial orientation during radial contraction of the stent.

Figure 7:
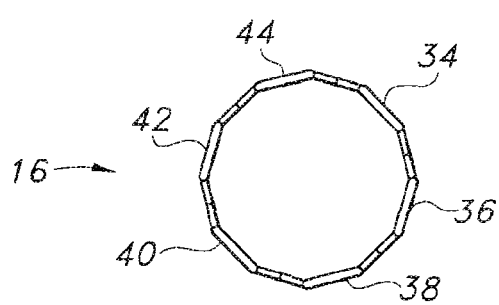
FIG. 7 is a proximal end view of the stent.

As illustrated in FIG. 7, loop segments 34-44 are arranged symmetrically about the proximal end of the stent, equally angularly spaced apart from one another. Radial contraction of stent 16 not only bends each loop segment into a narrower configuration, but also reduces the gaps between adjacent loop segments. The extent of permitted radial contraction is limited by the amount of bending permitted in each loop segment, particularly at the apex. A salient feature of the present invention is the association of single loop segments with pairs of strand junctions, which reduces the number of loops by one-half, as compared to the conventional loops formed by bending the strands at one end of the stent. Thus, the proximal end of stent 16, as compared to its distal end, is contractible to a smaller diameter.

Figure 8:
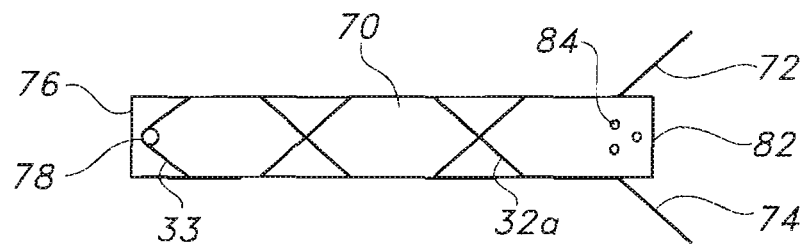
FIGS. 8-10 illustrate several stages in the fabrication of the stent.

Stent 16 is fabricated, first by helically winding strands 32 onto a shaping mandrel 70. While FIG. 8 shows only one strand 32a wound about the mandrel, it is to be appreciated that all of the strands are wound simultaneously onto the mandrel to form the braided structure. From a first end 72, strand 32a is wound helically about mandrel 70 until it approaches a remote end 76 of the mandrel, where the strand is trained about a pin 78 to form one of bends 33. Then, the strand is wound helically about the mandrel in the opposite direction, to a proximate end 82. Each strand forms two helical runs or passes over the axial length of the stent. In stent 16, twelve strands form twenty-four such runs. At the proximal end of the mandrel, the ends of the strands form twelve junctions 46.

Figure 9:
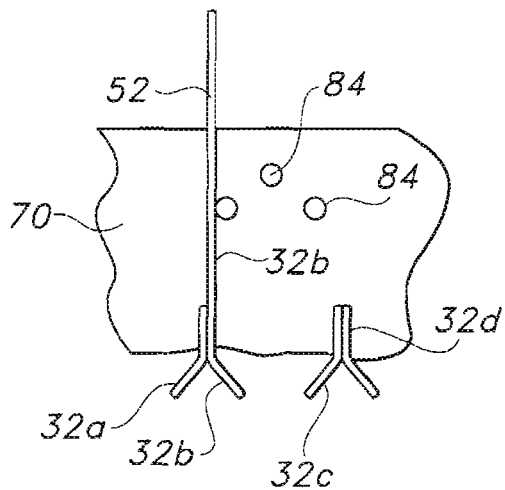
Figure 10:
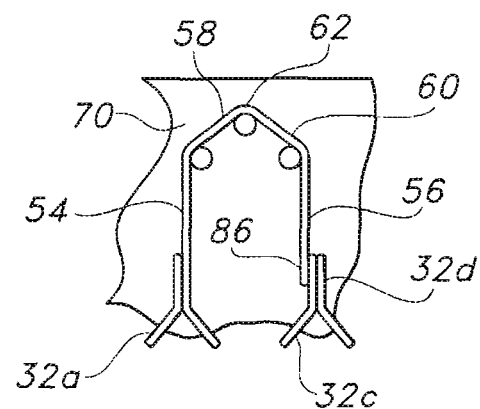

FIG. 9 shows two of the strand junctions, representing four strand ends, disposed on mandrel 70. Strand 32b includes portion 52 extending axially beyond the rest of the strands. Three pins 84 are fixed to the mandrel, axially outwardly of the strand couplings. Extension 52 of strand 32b is bent about each of pins 84. Its free end 86 is positioned against strand 32c, then attached to strand 32c by welding.

At this stage, mandrel 70 is placed in an oven (or the mandrel is heated) to a heat the strands to a heat set temperature. The heat set temperature, while much lower than the melting temperature for the strand material, is sufficient to relax the strands such that they are amenable to shaping. When the braided structure cools after heat setting, each strand retains its helical shape, and the strands cooperate to determine the relaxed-state tubular shape of the braided structure. Shape memory alloys such as Nitinol are particularly well suited for this process.

Figure 11:
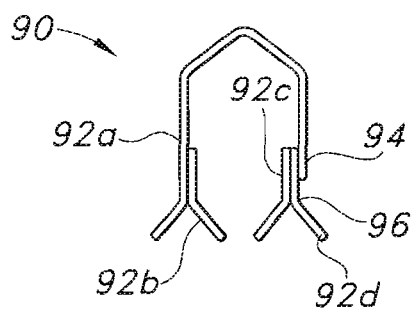
FIGS. 11-15 illustrate end regions of alternative embodiment prostheses.

FIG. 11 is a view similar to that in FIG. 6, showing part of a stent 90 with an alternative loop forming arrangement in which a strand 92a (rather than 92b) is longer than the other strands and provides the loop segment. In addition, a free end 94 of strand 92a is positioned adjacent strand 92d, rather than 92c, then welded to a junction 96b as before. This can be conveniently considered and "outside-to-outside" connection, as opposed to the "inside-to-inside" connection shown in FIG. 6. For stents of a given size, outside-to-outside connections form slightly wider loop segments.

Figure 12:
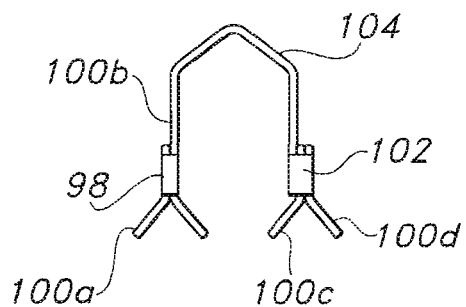

FIG. 12 shows another alternative arrangement in which hypotubes are used in lieu of welds to secure adjacent portions of the strands. The connections for one of the loop segments are formed by sliding a hypotube 98 over strands 100a and 10b, sliding a hypotube 102 over strands 100c and 100d, shaping an extension 104 of strand 100b and inserting its free end into hypotube 102, then crimping the hypotubes to provide a friction fit that anchors the strands to one another. The hypotubes preferably are formed of steel.

In similar alternative arrangements, tubes 98 and 102 can be formed of elastomeric materials and provide a friction fit, augmented with an adhesive if desired. In another alternative, tubes 98 and 102 are heat shrunk onto the adjacent strands.

Figures 13, 14:
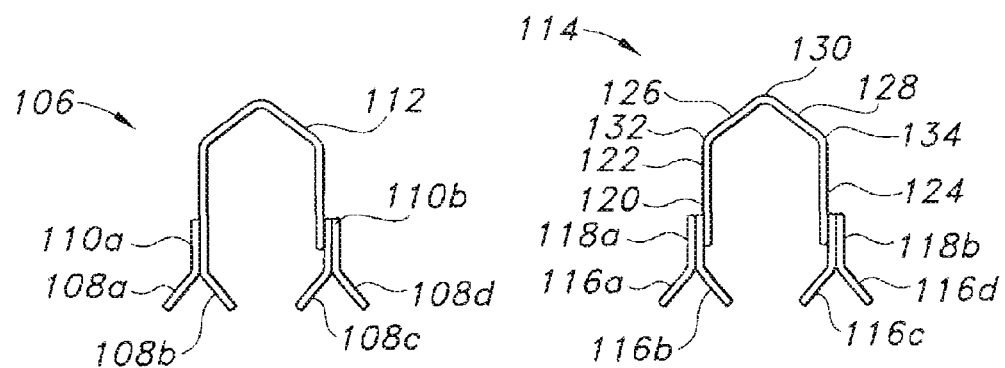

FIG. 13 shows part of the proximal end of a polymeric stent 106, specifically polymeric strands 108a and 108b forming a junction 110a, and polymeric strands 108c and 108d forming a junction 110b. The strand junctions are formed by fusion bonding. In addition, an extension 112 of strand 108b is shaped to provide a loop segment, and its free end is connected to strand 108c, again by fusion bonding. The fusion bonds are preferably formed simultaneously, although they can be formed serially.

FIG. 14 illustrates a proximal end region of an alternative stent 114 in which strands 116a and 116b are welded to form a strand coupling 118a, and strands 116 and 116d are welded into a strand coupling 118b. None of strands 116a-d extends axially beyond the others. Thus, none of strands 116 is shaped to provide end closure. Instead, loop closure is provided by a generally U-shaped strand segment 120. The strand segment includes counterparts to the elements described in connection with loop segment 34a, including opposed legs 122 and 124, side sections 126 and 128, an apex 130, and arcuate sections 132 and 134.

Strand segment 120 is attached to strand couplings 118a and 118b, by any of the previously mentioned connecting methods. This approach requires connections at both strand couplings. However, it facilitates using different materials for strands 116 and for strand segments 120 if desired, and also allows attachment of the strand segments to a previously formed stent.

Figure 15:
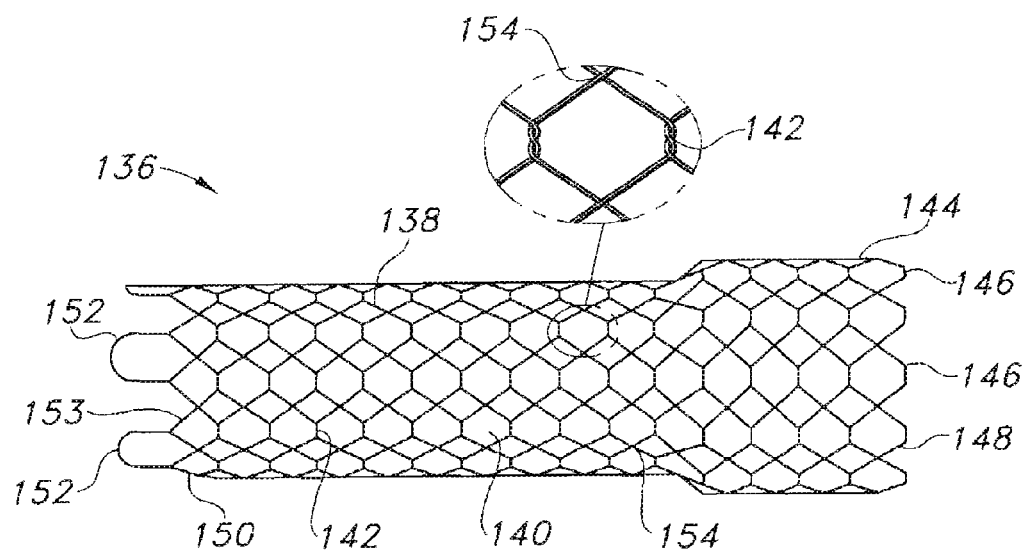

FIG. 15 illustrates an alternative embodiment open-frame prosthesis 136, in which elongate strands 138 are wound about a mandrel to form multiple, generally hexagonal cells 140. As indicated in the enlargement, adjacent cells are joined by coextensive regions 142 along which strands 138 are twisted helically about one another. At a distal end 144 of the prosthesis, the strands are bent to provide loops 146. A plurality of radiopaque markers 148 are fixed to the loops.

At a proximal end 150 of the prosthesis, pairs of strands 138 are welded together to form strand couplings. Each pair of adjacent couplings includes one strand with an extended portion shaped into a loop segment 152, which in turn is welded to the adjacent strand coupling of the pair. Radiopaque markers 153 are fixed near loop segments 152, and may be fixed to the loop segments. Strands 138 form multiple intersections 154 in addition to coextensive regions 142. Loop segments 152 can be arcuate as shown, or be shaped to more closely resemble loop segments 34-44.

Figure 16:
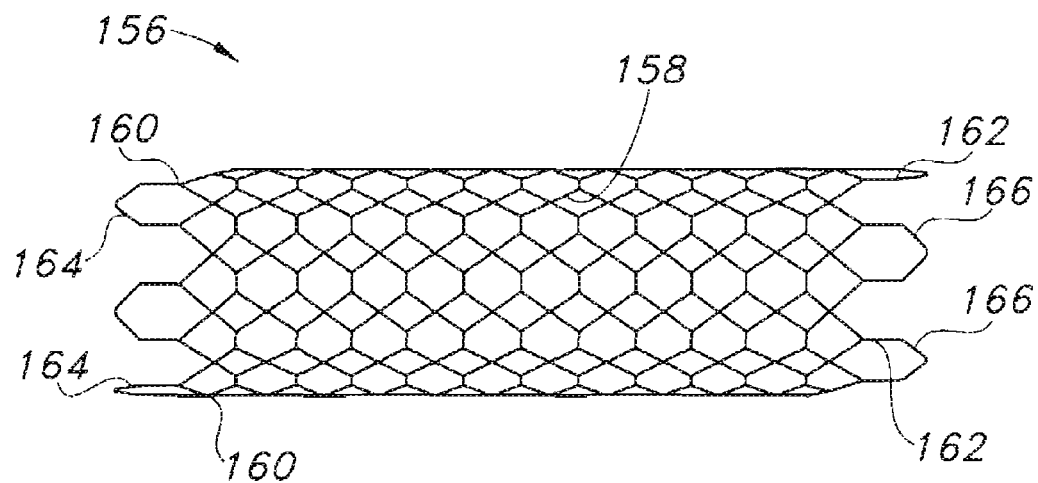
FIG. 16 is a side view of a further alternative embodiment prosthesis with welded loops at both ends.

FIG. 16 shows a braided prosthesis 156 formed of two sets of oppositely directed helically wound strands 158. At both ends of prosthesis 156, pairs of the strands are welded or otherwise secured together to form proximal end strand couplings 160, and distal end strand couplings 162. The prosthesis includes a plurality of proximal end loop segments 164. Each loop segment 164 is connected to an associated pair of the strand couplings 160. Prosthesis 156 includes a plurality of distal end loop segments 166, each coupled to an associated pair of the distal end strand couplings.

Figure 17:
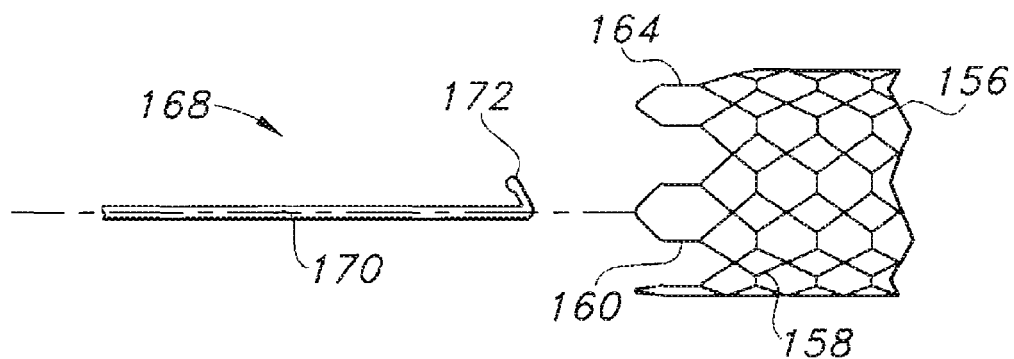
FIG. 17 illustrates a component for positionally adjusting or retrieving the stent of FIG. 16 after its deployment.

A salient feature of the present invention is that prostheses equipped with loop segments as previously described can be moved axially in either direction after they are deployed, with virtually no risk of trauma to surrounding tissue. FIG. 17 illustrates a proximal end region of prosthesis 156, and a positioning device 168 spaced apart proximally from the prosthesis. Device 168 includes an elongate flexible shaft 170, a distal portion of which is shown. A tine 172 at the distal end of shaft 170 extends away from the shaft, inclined proximally and radially outward. When shaft 170 is moved distally to position its distal end in proximate axial alignment with loop segments 164, the shaft is manipulated to direct tine 172 through one of the loops. Then the shaft is moved proximally to carry tine 172 into engagement with an associated loop segment 164, whereupon further proximal travel of the shaft pulls prosthesis 156 in the proximal direction.

Initially, only the proximal region of prosthesis 156 may be pulled proximally, which causes localized axial elongation. The axial elongation radially contracts prosthesis 156 along its proximal end region near the loop segments. This facilitates proximal movement of the prosthesis by pulling the prosthesis radially inward at least slightly away from the surrounding tissue. As device 168 is moved further in the proximal direction, the frictional hold is overcome and the entire prosthesis moves proximally, although a distal portion of the prosthesis may remain engaged with surrounding tissue. This is beneficial, in that the frictional "drag" allows a more incremental, accurate adjustment of prosthesis position.

For a symmetrical application of the pulling force, device 168 can be replaced with a device with several tines or shafts, to simultaneously pull several, or all, of the loop segments.

According to another alternative, a tether can be threaded through loop segments 164, such that proximally pulling the tether brings the loop segments radially inward and closer together in cinch fashion.

If desired, device 168 or the aforementioned tether can be used not only for incremental proximal adjustments, but for retrieval of prosthesis 156. To effect distal adjustments in the prosthesis position, a device similar to device 168, with a tine preferably inclined radially outwardly in the distal direction, could be used to engage one of distal end loop segments 166.

While the present invention has been disclosed primarily in connection with self-expanding stents and other open frame prostheses of tubular construction, it is readily apparent that a balloon-expandable prosthesis, or any other bodily insertable device with free wire ends, can be modified with loop segments as described to reduce the risk of trauma to tissue. Also, while the preferred embodiments involve strand couplings formed by joining pairs of strands, such couplings can be formed with three or more strands, then connected in pairs to the loop segments.

Thus, in accordance with the present invention, loop segments are attached to associated pairs of strand end couplings to reduce the risk of trauma to tissue, and provide a prosthesis that is radially compressible to a smaller diameter to facilitate intraluminal delivery. The looped ends eliminate the potential for adjacent twisted strand pairs to interlock when the prosthesis is compressed to its delivery state, ensuring a more reliable radial expansion of the prosthesis when deployed at the treatment site. The looped ends further facilitate incremental repositioning of the prosthesis after its deployment.

The invention claimed is:

1. An implantable prosthesis, comprising:
a plurality of elongate strands having first and second ends, said elongate strands interbraided to form an open-frame tubular structure having opposed first and second atraumatic ends;
wherein at said first atraumatic end, said elongate strands are bent to form bends;
wherein at said second atraumatic end, said elongate strands form a plurality of loops, each loop including extension strands and nonextension strands, wherein a portion of each of said extension strands extends beyond second ends of said nonextension strands,
   wherein there are at least first, second and third nonextension strands for every one associated extension strand;
   wherein the second ends of at least said first, said second and said third nonextension strands are coupled to said one associated extension strand at said second atraumatic end;
   wherein the second end of said first nonextension strand is attached to the second end of said second nonextension strand to form a pair of nonextension strands;
   wherein one end of said one associated extension strand is directly attached to said pair of nonextension strands to form said loop along said second atraumatic end of the tubular structure;
   wherein a number of said loops at said second atraumatic end is less than a number of said bends at said first atraumatic end.

2. The implantable prosthesis of claim 1, wherein the number of loops at said second atraumatic end is one half the number of bends at said first atraumatic end.

3. The implantable prosthesis of claim 1, wherein said open-frame tubular structure consists essentially of said plurality of elongate strands.

4. The implantable prosthesis of claim 1, wherein said plurality of elongate structural strands comprise metallic strands.

5. The implantable prosthesis of claim 1, wherein said plurality of elongate structural strands comprise polymeric strands.

6. The implantable prosthesis of claim 1, wherein said plurality of elongate structural strands comprise shape memory strands.

7. The implantable prosthesis of claim 6, wherein said shape memory strands comprise nitinol strands.

* * * * *